United States Patent
Fukuoka et al.

(10) Patent No.: US 7,317,046 B2
(45) Date of Patent: Jan. 8, 2008

(54) CYCLIC PHOSPHAZENES, PROCESS FOR PREPARING THEM, FLAME RETARDANT CONTAINING THEM AS ACTIVE INGREDIENT, AND RESIN COMPOSITION CONTAINING THEM AND MOLDED ARTICLE THEREFROM

(75) Inventors: Naohiko Fukuoka, Koube (JP); Heinosuke Yasuda, Koube (JP); Masayuki Nishimatsu, Koube (JP); Yoshinori Ohmae, Koube (JP)

(73) Assignee: Chemipro Kasei Kaisha, Limited, Koube (JP)

( * ) Notice: Subject to any disclaimer, the term of this patent is extended or adjusted under 35 U.S.C. 154(b) by 565 days.

(21) Appl. No.: 10/479,235

(22) PCT Filed: Jun. 5, 2002

(86) PCT No.: PCT/JP02/05554

§ 371 (c)(1),
(2), (4) Date: Dec. 1, 2003

(87) PCT Pub. No.: WO02/098886

PCT Pub. Date: Dec. 12, 2002

(65) Prior Publication Data

US 2004/0152910 A1  Aug. 5, 2004

(30) Foreign Application Priority Data

Jun. 5, 2001 (JP) ............................. 2001-170228
Jun. 5, 2001 (JP) ............................. 2001-170319

(51) Int. Cl.
*C08K 5/5399* (2006.01)
*C07F 9/02* (2006.01)

(52) U.S. Cl. ...................................... 524/116; 558/75
(58) Field of Classification Search .................. 558/75; 524/116
See application file for complete search history.

(56) References Cited

U.S. PATENT DOCUMENTS 5,652,285 A * 7/1997 Coggio et al. .............. 524/116

FOREIGN PATENT DOCUMENTS

JP  11-263885  *  9/1999

OTHER PUBLICATIONS

Fukuoka et al. 1999, CAS: 131:244114.*

* cited by examiner

*Primary Examiner*—Rei-tsang Shiao
(74) *Attorney, Agent, or Firm*—Oliff & Berridge, PLC

(57) ABSTRACT

The present invention relates to cyclic phosphazenes of general formula (1)

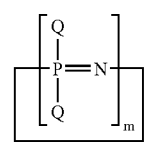

(1)

wherein Q is a halogen and/or an aryloxy group, and m is an integer of 3 to 10, which are characterized by being substantially free from linear phosphazenes of general formula (2)

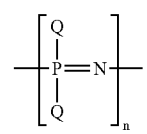

(2)

wherein Q is a halogen and/or an aryloxy group, and n is an integer of 1 to 20 and by having an extremely low content of halogen, and which are appropriate to flame retardants for resins; processes for preparing the same; flame retardants containing the same as an active ingredient; resin compositions containing the cyclic phosphazenes; and molded articles therefrom.

10 Claims, No Drawings

CYCLIC PHOSPHAZENES, PROCESS FOR PREPARING THEM, FLAME RETARDANT CONTAINING THEM AS ACTIVE INGREDIENT, AND RESIN COMPOSITION CONTAINING THEM AND MOLDED ARTICLE THEREFROM

This application is a 371 of PCT/JP02/05554 filed on Jun. 5, 2002.

TECHNICAL FIELD

The present invention relates to cyclic phosphazenes, a process for preparing them, a flame retardant containing them as an active ingredient, and a resin composition containing them and a molded article therefrom.

BACKGROUND ART

One of the prior processes for preparing cyclic aryloxy phosphazenes is a process of Yokoyama (Journal of the Chemical Society of Japan, Vol. 80, No. 10, p. 118 (1959)) in which phosphorus pentachloride is reacted with ammonium chloride in monochlorobenzene to produce a mixture of cyclic chlorophosphazenes represented by formula (3)

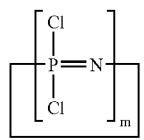
(3)

wherein m is a integer of 3 to 10, with linear chlorophosphazenes represented by formula (4)

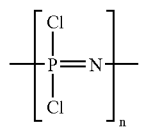
(4)

wherein n is an integer of 1 to 20; and the mixture of cyclic and linear chlorophosphazenes is recrystallized in a petroleum ether, etc. to produce chlorophosphazenes represented by formula (3)

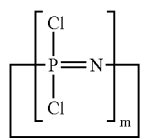
(3)

wherein m is an integer of 3 to 10; and the chlorophosphazenes are reacted with phenols to produce cyclic aryloxyphophazenes. Concretely, Yokoyama (Journal of the Chemical Society of Japan, Vol. 81, No. 3, p. 481 (1960)) reports on a condensation reaction of triphosphonitrile chloride with alkaline metal phenolates in the presence of pyridine as catalyst.

In addition, Japanese Patent Laid-open No. Sho 58-219190 discloses polyhydroxyphenyl phosphonitrilate bearing phenolic hydroxy groups characterized by containing substantially no polycondensation products and no residual chlorine; and a process for preparing the same. This relates to polyhydroxyphenyl phosphonitrilate bearing phenolic hydroxy groups and a process for preparing the same characterized by comprising reacting a phosphonitrile halide with a sodium or potassium salt of a monomethoxy phenol obtained by protecting one hydroxy group of a dihydric phenol with methyl group to produce polyhydroxyphenyl phosphonitrilate, and then reacting the phosphonitrilate with a pyridine hydrohalogenic acid to convert the methoxy moiety into a hydroxy group.

The present inventors disclose in Japanese Patent Laid-open No. 2001-2691 a process for preparing a cyclic phosphazene comprising reacting a cyclic halogenated phosphazene with an alkaline metal phenolate in a solvent containing nitrogen-containing linear and/or cyclic organic compound.

In the prior processes for preparing cyclic aryloxyphosphazenes, isolated cyclic chlorophosphazene is used as a raw material. When cyclic chlorophosphazenes are obtained in an industrially large amount from a mixture of cyclic and linear chlorophosphazenes, a large quantity of halogen gas may be generated and pollute remarkably the environment, and results in very low workability. Even though isolated and purified cyclic chlorophosphazenes are reacted with a phenol, the intended cyclic phosphazene is not prepared because linear phosphazenes are given by ring-opening of cyclic phosphazenes during the reaction, unsubstituted phosphazenes having chlorine may remain, or linear phosphazenes are given by the hydrolysis of cyclic phosphazenes during its after-treatment.

Phenyl phosphonitrilates prepared by the process described in Journal of the Chemical Society of Japan, Vol. 81, No. 3, p. 481 (1960) are not solid but yellow viscous liquid as they contain linear phosphazenes prepared by ring-opening of cyclic phosphazenes, or unsubstituted phosphazenes having chlorine, and the phosphonitrilates cannot be purified.

A preparation process disclosed in Japanese Patent Laid-open No. 2001-2691 discloses phosphazenes containing lower content of halogen compared with the conventional processes, but the content of halogen is as much as about 100 ppm. In addition, as cyclic halogenated phosphazenes are used as a raw material, it is unavoidable to result in linear phosphazenes due to ring-opening of a part of the cyclic phosphazenes during the reaction.

In addition, in Japanese Patent Laid-open No. Sho 58-219190 described above, a sodium salt of monomethoxy phenol is used in an amount by a factor of 1.1 based on 1 of chlorine in phosphonitrile halide and the reaction is carried out. However, the reaction is not completed and thus unsubstituted organic halides remain. Consequently, although phosphazenes represented by the above-mentioned general formula (1) contain no halogen in the structural formula thereof, all substituents thereon cannot be necessarily substituted with aryloxy groups, so that halogens still remain on a part of the resulting compounds in the structural formula thereof. In particular, it is difficult to substitute the finally remaining one halogen on a compound, and it is not able to completely substitute even when the reaction is carried out for about 250 hours.

Consequently, although the phosphazenes represented by the above-mentioned general formula (1) are cyclic on the structural formula thereof, the cyclic structure on the above-mentioned general formula (1) cannot be necessarily maintained in the conventional preparation processes, therefore a part of the products becomes linear compounds.

Additives for resin include flame retardants, UV light absorbers, antioxidants, plasticizers, nucleating agents, etc. Needless to say, they have to satisfy several requirements, for example they do not deteriorate stability during fabrication nor pollute molds, further they affect no adverse influence on products, in particular they cause no breed-out that they exude from the surface of resins.

In particular, recently it has become problems that flame retardant compositions containing a resin and a flame retardant in which halogen-containing compounds that have been conventionally main substances for the flameproofing of wires or cables, etc. are used alone or an admixture with antimony compounds, such as antimony oxide generate halogen gas when the compositions are subjected to combustion or molding process, etc. It is further said that the generated gas often deteriorates electrical properties or transmission properties. Therefore, there has been a growing demand for a flame retardant resin composition that generates no halogen gas when it subjected to combustion or molding process, etc.

In order to fulfill these demands, for recent years metal hydrates or phosphorus flame retardants (phosphate esters, ammonium polyphosphates, phosphazenes, etc.) have been used as non-halogen flame retardants.

Metal hydrates, such as aluminum hydroxide or magnesium hydroxide have been regarded to improve a flame retardant effect because endothermic reaction due to dehydration and thermal decomposition of the metal hydrates at a combustion temperature of a resin occurs within a temperature range overlapping with a temperature at which a resin starts thermal decomposition or combustion. However, as the effect affording flame retardance by the metal hydrates alone is not very high, they have to be added in a large quantity, thereby resulting in defects that molded products are adversely affected on the mechanical properties thereof.

The conventional phosphorus flame retardants have excellent properties that act as plasticizers or antioxidants by adding to a resin in addition to inherent flame retardant effect. However, as triarylphosphates, such as triphenylphosphate, tricresylphosphate or cresyldiphenylphosphate have a low boiling temperature, they have defects that they vaporize during the molding process and thus pollute molds or they cause breed-out which they exude from the surface of resins. Condensed phosphate esters resolve the above-mentioned defects. However, when the catalysts used in the preparation of the phosphate esters remain therein, it is known that they result in a lowering of performance due to decomposition of not only the phosphate esters but also resins during the molding process and that the phosphate esters gel, thereby causing a remarkable lowering in productivity. Ammonium polyphosphates have a low heat-stability and thus impose restraints on processing conditions. In addition, as ammonium polyphosphates have a low content of phosphorus, they have also a defects that have to be added in a large quantity.

An object of the present invention is to provide cyclic phosphazenes which solve the defects in the prior technology as mentioned above, can be produced without repeated purification, have an extremely low content of halogen and have a low content of linear phosphazenes; novel processes for preparing the same; flame retardants containing the same as an active ingredient; and resin compositions, containing the cyclic phosphazenes and molded articles therefrom.

DISCLOSURE OF INVENTION

In this connection, the present inventors studied intently on reaction conditions and purification conditions under which products substantially free from linear phosphazenes can be produced in the preparation of phosphazenes, and consequently found that linear phosphazenes act as an excellent crystallization solvent and dissolve unsubstituted halogen-containing phosphazenes, and then cyclic phosphazenes having an extremely low content of halogen and an extremely low content of linear phosphazenes can be produced by reacting a mixture of cyclic and linear halogenated phosphazenes with alkaline metal phenolate to produce a mixture of cyclic and linear aryloxyphosphazenes and separating and purifying the mixture by crystallization, and that the cyclic phosphazenes free from linear phosphazenes have higher flame retardant effect than mixtures of cyclic phosphazenes and linear phosphazenes, and the inventors completed the present invention.

A first aspect of the present invention relates to cyclic phosphazenes of general formula (1)

wherein Q is a halogen and/or an aryloxy group, and m is an integer of 3 to 10, which are characterized by being substantially free from linear phosphazenes of general formula (2)

wherein Q is a halogen and/or an aryloxy group, and n is an integer of 1 to 20.

A second aspect of the present invention relates to the cyclic phosphazenes according to claim 1, wherein a content of the linear phosphazenes is 5.0% by weight or less.

A third aspect of the present invention relates to cyclic phosphazenes of general formula (1)

wherein Q is a halogen and/or an aryloxy group, and m is an integer of 3 to 10, which are produced by separating and purifying a phosphazene composition comprising the cyclic phosphazenes of general formula (1) and linear phosphazenes of general formula (2)

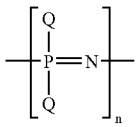

(2)

wherein Q is a halogen and/or an aryloxy group, and n is an integer of 1 to 20.

A fourth aspect of the present invention relates to the cyclic phosphazenes according to any one of claims 1 to 3, wherein Q in general formula (1) is an aryloxy and the cyclic phosphazenes are substantially free from halogen.

A fifth aspect of the present invention relates to the cyclic phosphazenes according to claim 4, wherein a content of the halogen is 50 ppm or less.

A sixth aspect of the present invention relates to a process for preparing the cyclic phosphazenes according to any one of claims 1 to 5, characterized by separating and purifying cyclic phosphazenes of general formula (1)

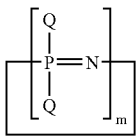

(1)

wherein Q is a halogen and/or an aryloxy group, and m is an integer of 3 to 10, by crystallization from a phosphazene composition comprising the cyclic phosphazenes of general formula (1) and linear phosphazenes of general formula (2)

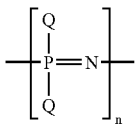

(2)

wherein Q is a halogen and/or an aryloxy group, and n is an integer of 1 to 20.

A seventh aspect of the present invention relates to a process for preparing the cyclic phosphazenes according to claim 4 or 5, characterized by separating and purifying cyclic phosphazenes of general formula (1)

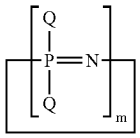

(1)

wherein Q is a halogen and/or an aryloxy group, and m is an integer of 3 to 10, by crystallization from a phosphazene composition comprising the cyclic phosphazenes of general formula (1) and linear phosphazenes of general formula (2)

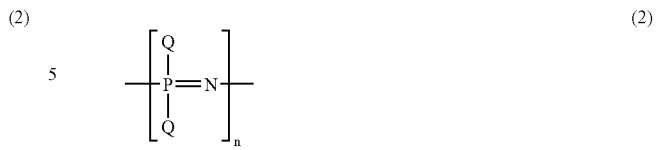

(2)

wherein Q is a halogen and/or an aryloxy group, and n is an integer of 1 to 20.

An eighth aspect of the present invention relates to a flame retardant composition containing the cyclic phosphazenes according to any one of claims 1 to 5 as an active ingredient.

A ninth aspect of the present invention relates to a resin composition characterized by containing the cyclic phosphazenes according to any one of claims 1 to 5.

A tenth aspect of the present invention relates to a molded article characterized by being molded from the resin composition according to claim 9.

In brief, the cyclic phosphazenes of the present invention are the cyclic phosphazene compound of general formula (1) and a mixture thereof, and are characterized by being substantially free from linear phosphazenes of genera formula (2).

A mixture of cyclic and linear aryloxyphosphazenes used in the present invention is produced by reacting a mixture of cyclic and linear halogenated phosphazenes with phenols according to a known method. For example, a mixture solution of cyclic and linear halogenated phosphazenes or a solution of cyclic halogenated phosphazenes is added dropwise to a slurry of alkaline metal phenolate and reacted together.

The mixture of cyclic and linear halogenated phosphazenes that is a raw material for producing a mixture of cyclic and linear aryloxyphosphazenes used in the present invention is not specifically limited as long as it is, for example a mixture of cyclic halogenated phosphazenes of general formula (3) and linear halogenated phosphazenes of general formula (4). The mixture of cyclic and linear aryloxyphosphazenes is produced depending on the values of m and n in the compounds of general formulae (3) and (4) as raw materials.

The present invention provides cyclic aryloxyphosphazenes having an extremely low content of halogen and also an extremely low content of linear aryloxyphosphazenes by crystallizing a mixture of cyclic and linear aryloxyphosphazenes in a solvent containing aromatic nonpolar solvent. Strange to say, however, the content of halogen is not reduced when cyclic aryloxyphosphazenes are purified in a similar manner. It is assumed from this fact that linear aryloxyphosphazenes act as a solvent for dissolving selectively aryloxyphosphazenes containing halogen, thereby resulting in an excellent purification effect.

In particular, the purification method of the present invention is a very effective method for obtaining cyclic aryloxyphosphazenes having an extremely low content of halogen from a phosphazene mixture in which halogen components remain because of incomplete condensation reaction of a mixture of cyclic and linear halogenated phosphazenes with phenols.

The present invention provides cyclic aryloxyphosphazenes having an extremely low content of linear aryloxyphosphazenes by crystallizing a mixture of cyclic and linear aryloxyphosphazenes in a solvent containing aromatic nonpolar solvent. In the meanwhile, a conventional decolorization, such as a treatment with active carbon or white earth may be carried out in the preparing process of the present invention.

The above-mentioned aryloxy includes, for example phenyloxy that is unsubstituted or substituted with a halogen, methyl, ethyl, n-propyl, iso-propyl, tert-butyl, tert-octyl, 2,3-dimethyl, 2,4-dimethyl, 2,5-dimethyl, 2,6-dimethyl, 3,5-dimethyl, hydroxy, methoxy, ethoxy, n-propoxy, iso-propoxy, phenyl, etc.

The above-mentioned alkaline metal phenolates may be used alone or in a mixture of two or more. When two kinds of the phenolates are used, it is natural that products have two kinds of aryloxy groups.

The cyclic phosphazenes of general formula (1) include the following compounds. For example, in a case where m is 3,

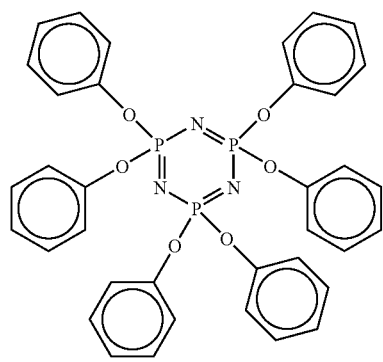
(5)

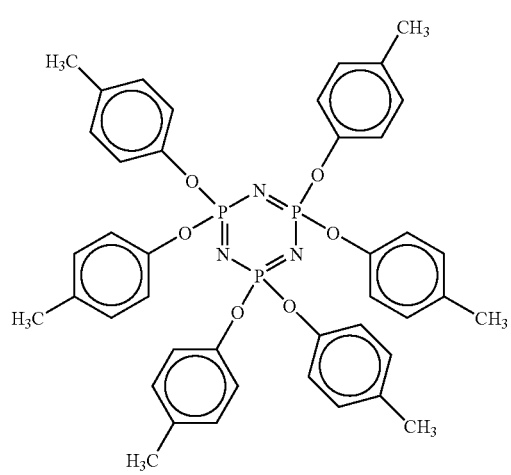
(6)

-continued

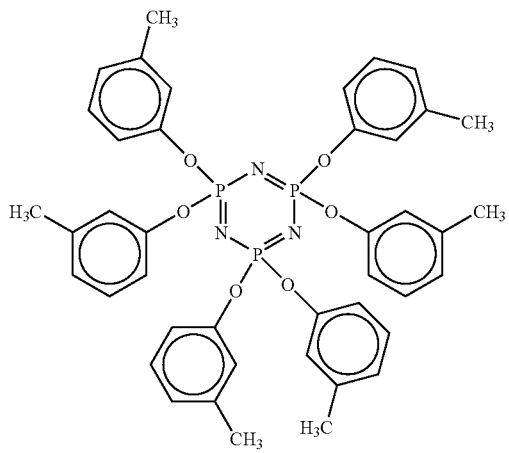
(7)

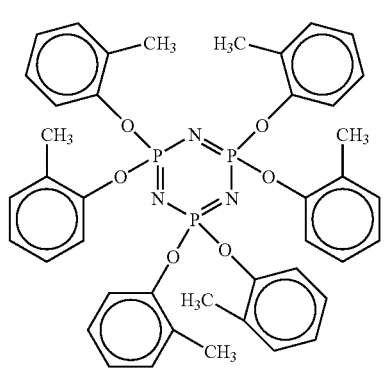
(8)

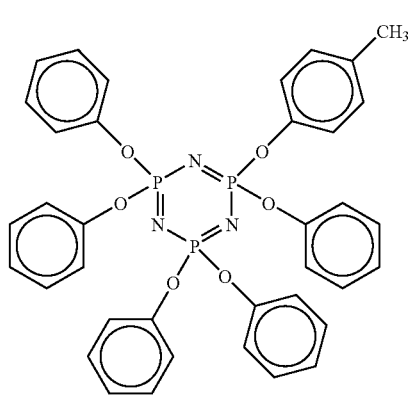
(9)

(10)

(11) 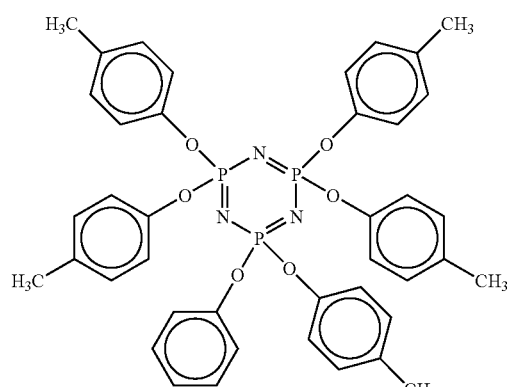
(12) 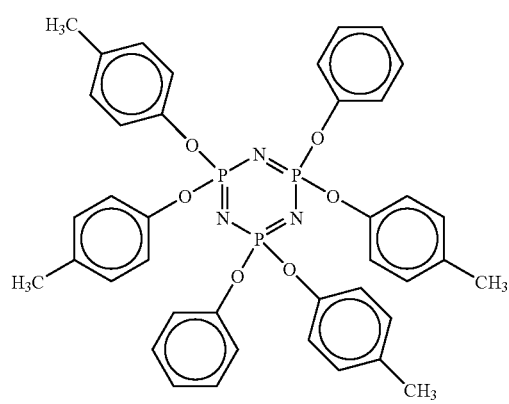
(13) 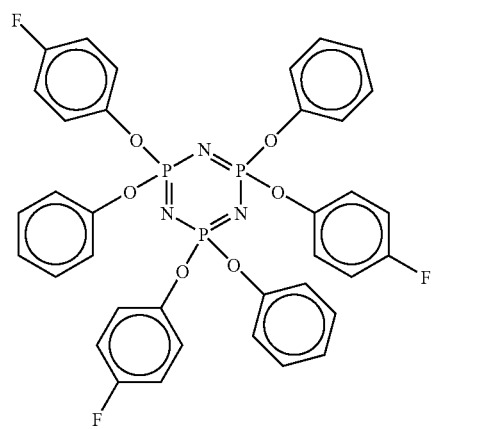
(14) 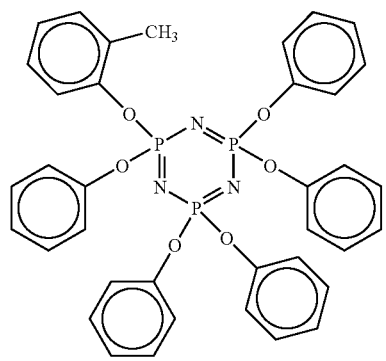
(15) 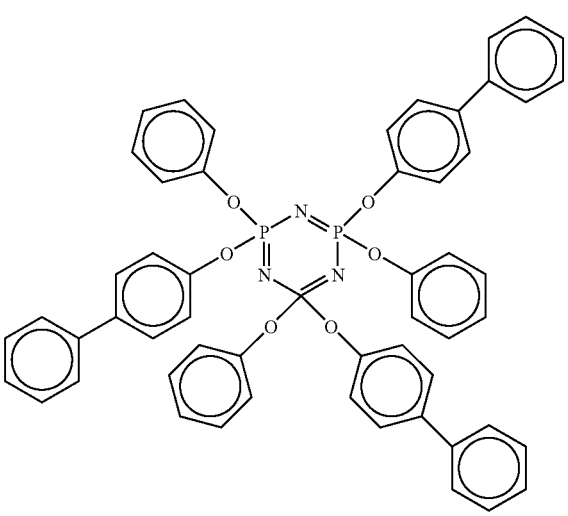
(16) 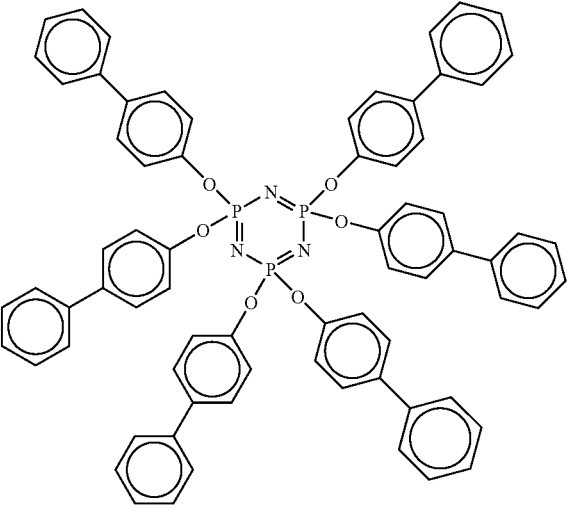
(17) 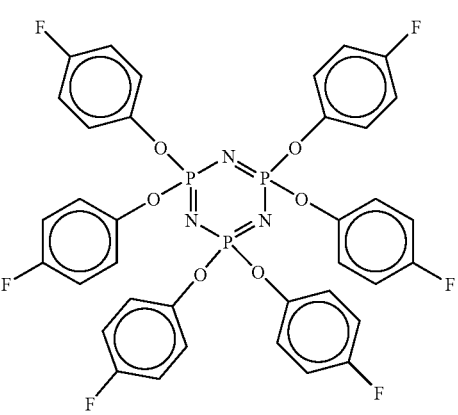

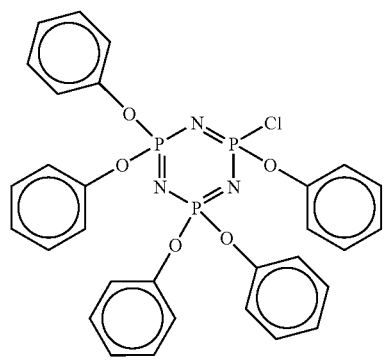
(18)
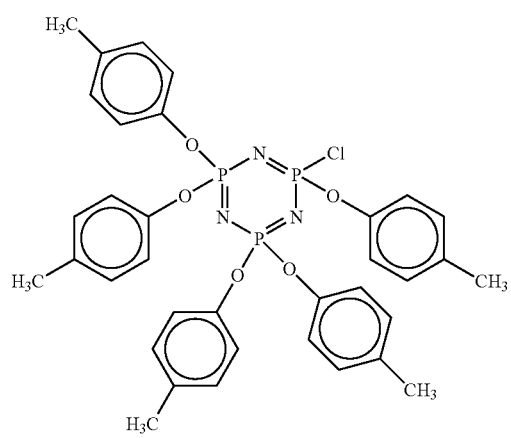
(19)
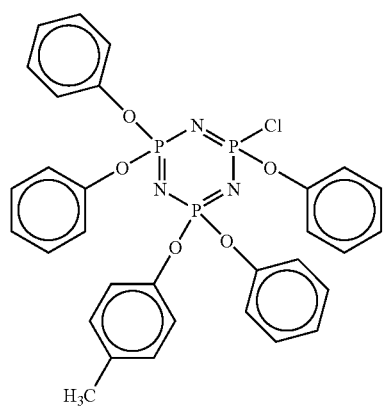
(20)
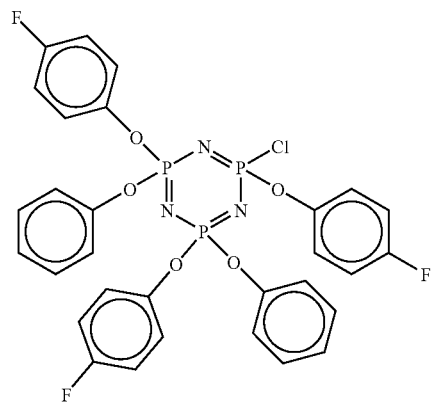
(21)
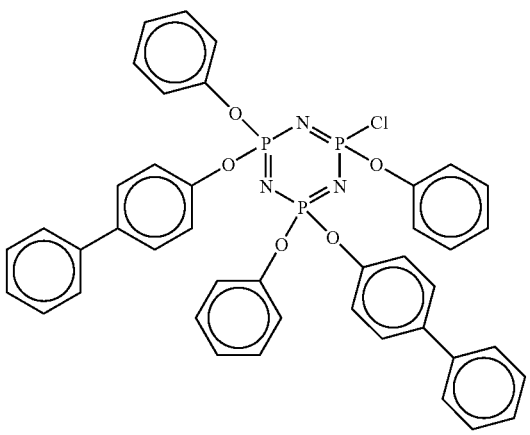
(22)
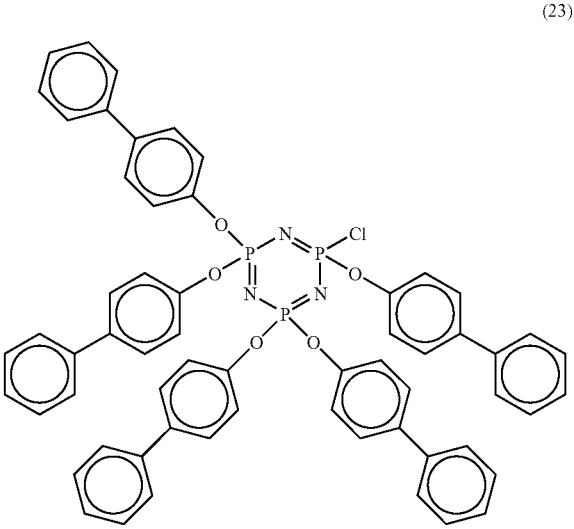
(23)
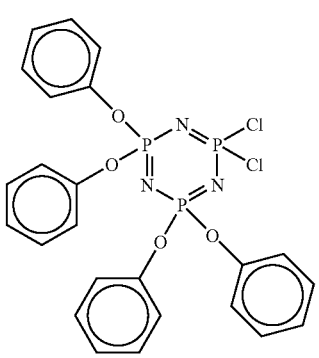
(24)

(25)
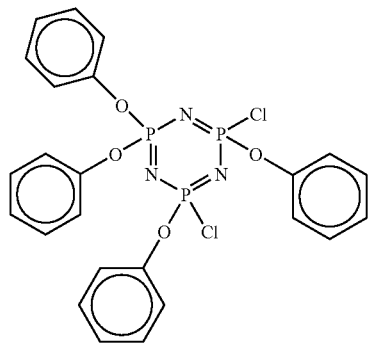
(26)
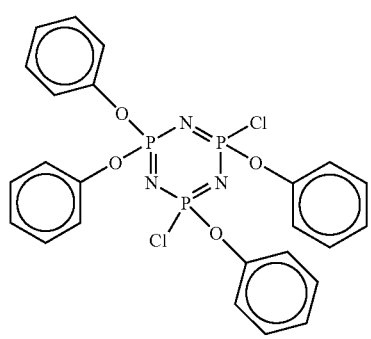
(27)
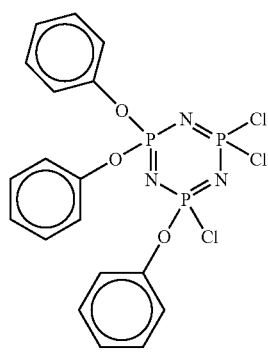
(28)
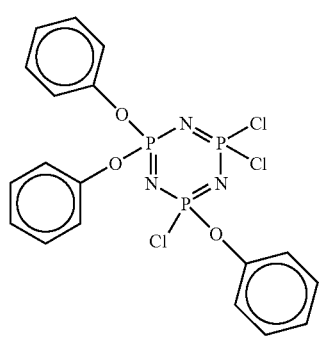
(29)
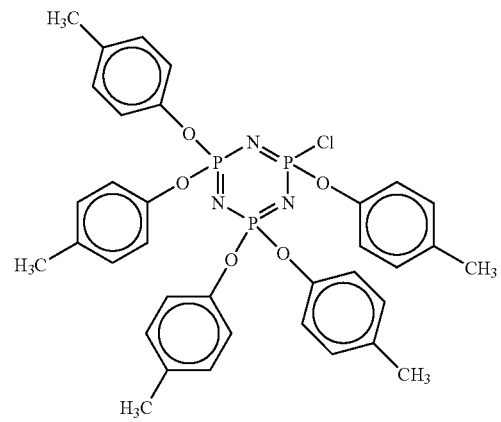
(30)
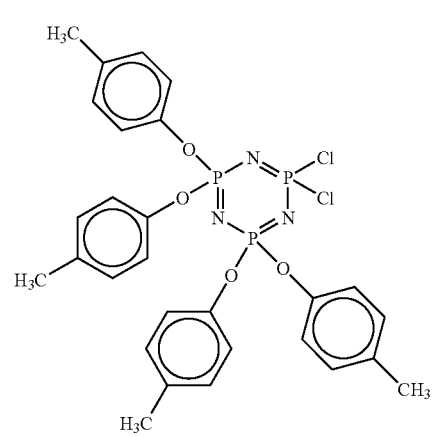
(31)
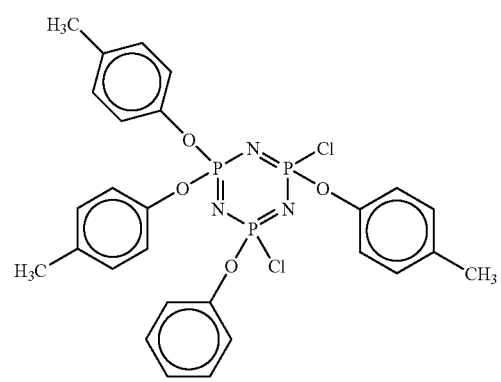
(32)
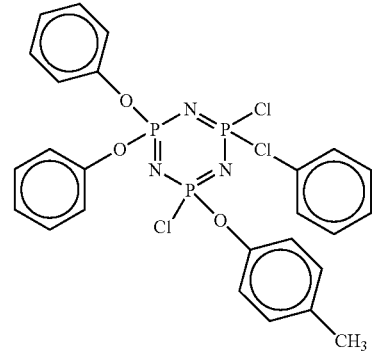

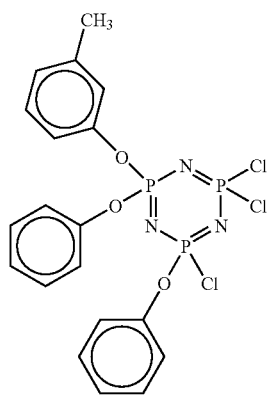
(33)
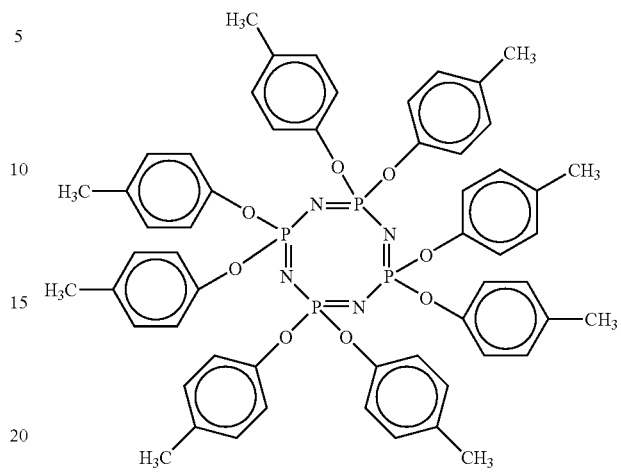
(36)
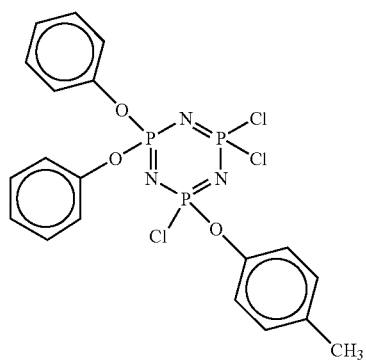
(34)
In a case where m is 4 or 5,
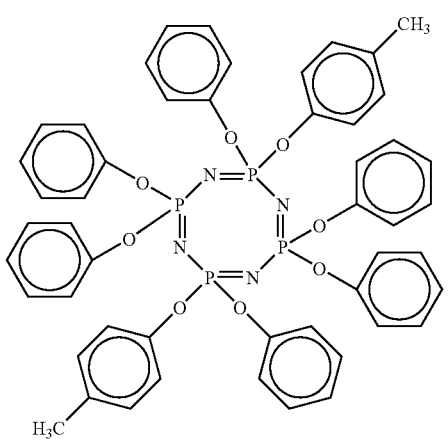
(37)
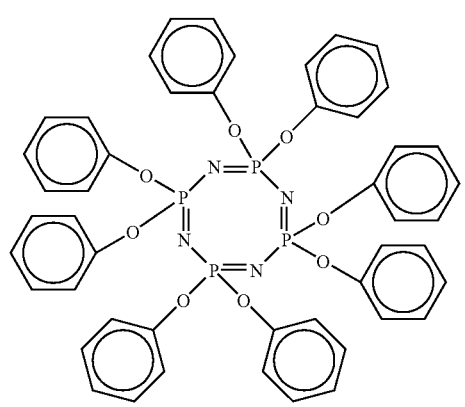
(35)
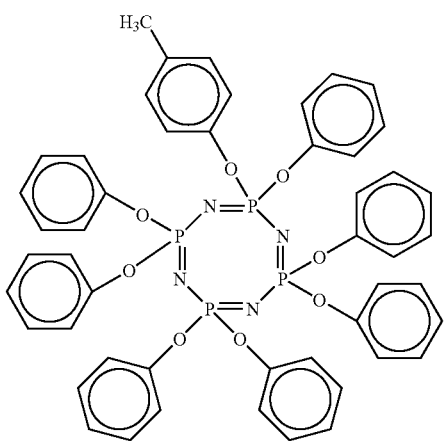
(38)

-continued
(39)
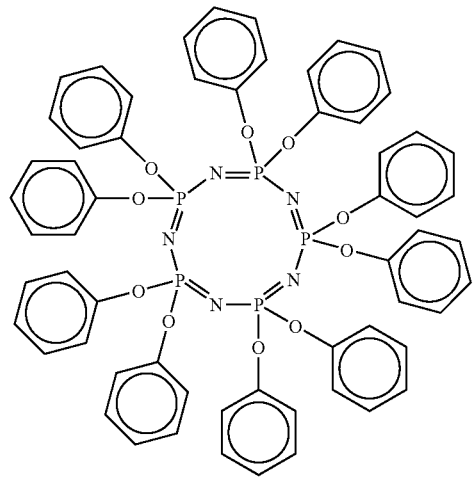
(40)
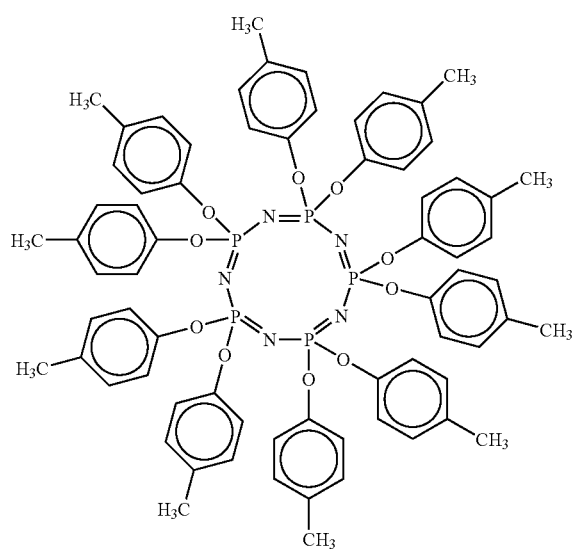
(41)
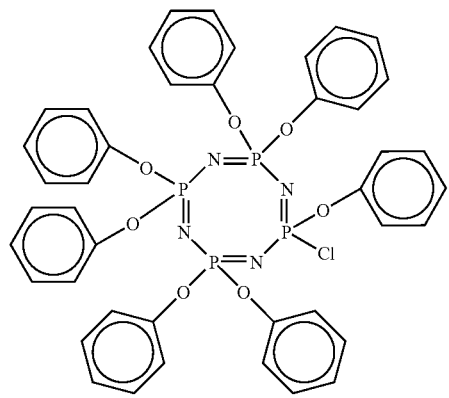
-continued
(42)
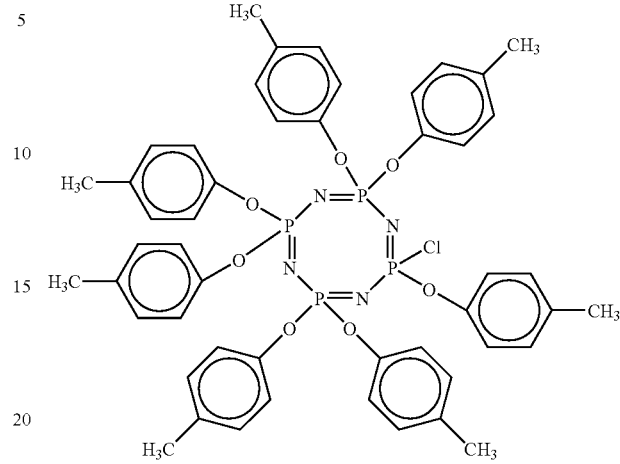
(43)
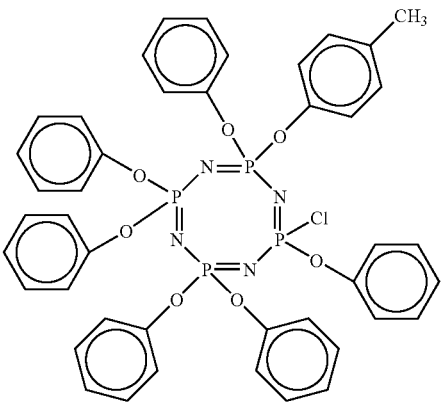
(44)
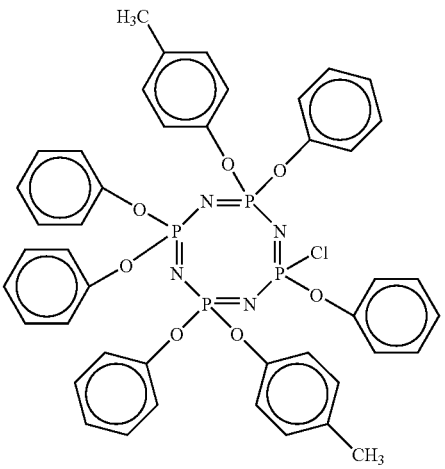

(45)

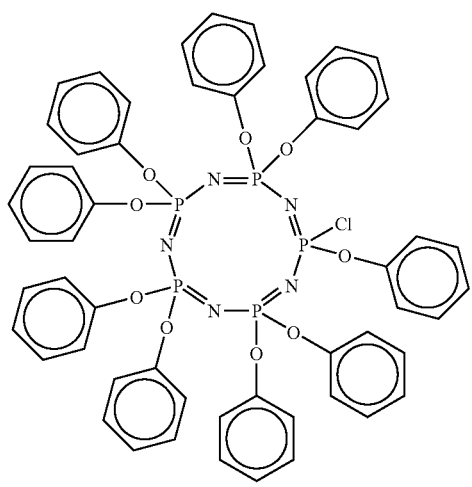

(46)

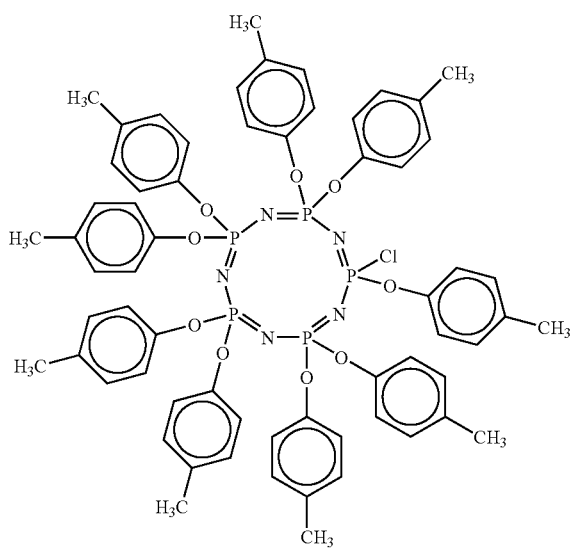

In the crystallization of phosphazenes in the present invention, commonly used dispersants or ion exchange resins may be added therein.

The dispersants include tetramethylammonium chloride, tetraethylammonium chloride, tetrabutylammonium bromide, tetrabutylammonium hydroxide, tetrabutylammonium hydrogen sulfate, tetralaurylmethylammonium chloride, dihardened tallow alkyldimethylammonium acetate, trimethylphenylammonium chloride, benzyl trimethylammonium chloride, cetyl trimethylammonium chloride, stearyl trimethylammonium chloride, distearyl dimethylammonium chloride, etc.

The ion exchange resins include Amberlite IR-116, IR-118 (H), IR-120B, IR-122, IR-124 (trade name, Organo Corp.) and Amberlist 15, A-26, A-27, A-21, 252, 200C, 200CT, IRC-50, IRC-84, IRC-718, IRA401, IRA-402, IRA400 (trade name, Organo Corp.), etc.

The flame retardant of the present invention is expected to exert a further flame retardant effect by using a mixture of the above-mentioned phosphazenes or a mixture with other flame retardants.

The other flame retardants that may be added to the flame retardant of the present invention include metal hydroxides, silicates, organic silicon compounds, fluorine resins, inorganic flame retardants, phosphorus flame retardants, halogen flame retardants and nitrogen flame retardants, and they may be used in a mixture thereof.

The metal of the metal hydroxides that may be added to the flame retardant of the present invention includes metals belonging to Groups 2 and 13 of the periodic table (corresponding to Groups 2 and 13 among Groups 1 to 18 in new IUPAC format, that is Groups IIa and IIIb of the former periodic table) and zinc, and preferably magnesium and aluminum. These metal hydroxides may be used alone or ones covered with an organic compound, such as a higher aliphatic carboxylic acid, a hydrogenated oil or a salt of a higher aliphatic carboxylic acid in which metal belongs to Groups 1, 2, 12 or 13 of the periodic table (corresponding to Groups 1, 2, 12 or 13 among Groups 1 to 18 in new IUPAC format, that is Groups Ia, IIa, IIb or IIIb of the former periodic table). The metal hydroxides, particularly magnesium hydroxide are on the market in the name of KISUNA-5A, 5B, 5E or 5J (trade name, produced by Kyowa Chemical Industry Co., Ltd.), Magseeds N-3, N-1, Standard type 200, 10 or 10A, Starmag UM, M, L, S, C or CY (trade name, produced by Konoshima Chemical Co., Ltd.) or FR-200 (trade name, produced by Bromochem Far East Co.) and they may be used as such.

The silicates that may be added to the flame retardant of the present invention include, for example, sodium silicate, sodium metasilicate, sodium orthosilicate, water glass, magnesium silicate, potassium silicate, potassium magnesium silicate, calcium silicate, aluminum silicate, zirconium silicate, silicate-molybdate, forsterite or olivine, cyclic silicates, such as wollastonite or beryl, linear silicates, such as enstatite, lithium augite or hornblende, etc., layer silicates, such as mica or clay minerals, etc., three-dimensional silicates, such as silicon dioxide, orthoclase or zeolite, etc.

The organic silicon compounds that may be added to the flame retardant of the present invention includes, for example, alkoxy silanes, such as tetramethoxysilane, tetraethoxysilane, tetrapropoxysilane, trimethoxysilane, triethoxysilane, tripropoxysilane, methyltrimethoxysilane, methyltriethoxysilane, methyltripropoxysilane, phenyltrimethoxysilane, phenyltriethoxysilane, dimethoxymthylphenylsilane, dimethoxy-3-mercaptopropylmethylsilane, 3-mercaptopropyltrimethoxysilane, 3-aminopropyldiethoxymethylsilane, 3-(2-aminoethylaminopropyl)trimethoxysilane, 3-(2-aminoethyl-aminopropyl)dimethoxymethylsilane, 3-glysidopropyltrimethoxysilane, 3-methacryloxypropyltrimethoxysilane or diethoxy-3-glysidoxypropylmethylsilane, polysloxanes, such as dimethylpolysiloxane, methylhydrogenpolysiloxane or methylphenylpolysiloxane, alkyl, amino, epoxy, carboxyl, mercapto, alcohol, alkyl higher alcohol esters, polyethers, alkylaralkylpolyether modified silicones.

The fluorine resins that may be added to the flame retardant of the present invention include, for example, polytetrafluoroethylene resin (PTFE), tetrafluoroethylene-hexafluoropropylene copolymer resin (FEP), tetrafluoroethylene-perfluoroalkylvinylether copolymer resin (PFA), tetrafluoroethylene-ethylene copolymer resin (ETFE), poly(chloro-trifluoro ethylene) (CTFE) or poly(vinylidene fluoride) (PVDF), etc.

The inorganic flame retardants that may be added to the flame retardant of the present invention include, for example, diantimony trioxide, diantimony tetraoxide, diantimony pentoxide, sodium antimonate, zinc borate, magnesium oxide or calcium oxide, etc.

The phosphorus flame retardants that may be added to the flame retardant of the present invention include, for example, red phosphorus, ammonium polyphosphate, triphenylphosphate, triethylphosphate, trimethylphosphate, tricresylphosphate, trixylenylphosphate, cresylphenylphosphate, tris(3-hydroxypropyl)phosphine oxide, glycidyl-α-methyl-β-dibutoxyphosphinyl propionate, dibutylhydroxymethylphosphonate, dibutoxyphosphinylpropylamide, dimethylmethylphosphonate, di(polyoxyethylene)hydroxymethylphosphonate or aromatic condensed phosphates, etc.

Red phosphorus may be used alone or one covered with an appropriate inorganic or organic compound, or one diluted with non-halogen organic polymer composition. They are on the market in the name of Nova Red 120, 120UF, 120UFA, Nova Excel ST, W, MG, RX series, several products under Nova Pallet (produced by Rinkagaku Kogyo Co., Ltd.), Hishi Guard CP, CP-15, UR-15, TP-10, Safe TP-10 (produced by Nippon Chemical Industrial), PR-120 (produced by Suzuhiro Chemical Co., Ltd.) and they may be used as such.

The halogen flame retardants that are optionally added to the flame retardant of the present invention include, for example, tris(chloroethyl)phosphate, tris(dichloropropyl)phosphate, bis(2,3-dibromopropyl)-2,3-dichloropropylphosphate, tris(2,3-dibromopropyl)phosphate, bis(chloropropyl)mono-octylphosphate, hexabromobenzene, hexabromobiphenylether, tribromophenol, tetrabromo bisphenol A, tetrabromo phthalic anhydride, hexabromocyclodecane, bis(bromoethylether) tetrabromo bisphenol A, ethylenebistetrabromophthalimide, brominated epoxy oligomer, brominated polystyrene, decabromodiphenylethane, brominated aromatic triazine, tetrabromoethane, octabromotrimethylphenylindane, polydibromophenylene oxide, pentabromobenzyl acrylate, pentabromobenzyl polyacrylate, bis(tribromophenoxy)ethane, dibromocresylglycidyl ether, dibromophenylglycidyl ether, tetrabromophthalate diol tetradibromophthalate ester, etc.

The nitrogen flame retardants that may be added to the flame retardant of the present invention include, for example, guanidine sulfamate, guanidine phosphate, guanyl urea phosphate, melamine phosphate, dimelamine phosphate, melamine borate, melamine cyanurate, and hindered amine flame retardants include TINUVIN 123, TINUVIN XT, TINUVIN NOR 371, Flamestab NOR 116, TINUVIN 770, TINUVIN 622, CHIMASSORB 944, CHIMASSORB 119, CHIMASSORB 2020, etc.

The flame retardant of the present invention may contain further, for example, commonly used additives, such as fillers, reinforcing agents for plastic, lubricants, etc.

The fillers that may be added to the flame retardant of the present invention include, for example, calcium carbonate, titanium oxide, clay, calcined clay, silane-treated clay, talc, mica, silica, wollastonite, bentonite, diatomaceous earth, silica sand, ground pumice, slate flour, alumina white, aluminum sulfate, barium sulfate, lithopone, calcium sulfate, molybdenum disulfide, surface treated filler, reclaimed rubber, rubber powder, ebonite powder, shellac, etc.

The reinforcing agents for plastic that may be added to the flame retardant of the present invention include, for example, mica powder, graphite, glass fiber, glass beads, volcanic glass hollow sphere, carbon fiber, carbon hollow body, smokeless charcoal powder, synthetic cryolite, silicone resin powder, silica spherical fine particle, polyvinyl alcohol fiber, aramid fiber, alumina fiber, high-strength polyacrylate fiber, etc.

The lubricants that may be added to the flame retardant of the present invention include, for example, paraffin wax, liquid paraffin, paraffin synthetic wax, polyethylene wax, composite wax, montan wax, silicone oil, stearic acid, lithium stearate, sodium stearate, magnesium stearate, potassium stearate, aluminum stearate, calcium stearate, zinc stearate, hydroxy stearic acid, magnesium 12-hydroxy stearate, calcium 12-hydroxy stearate, barium 12-hydroxy stearate, zinc 12-hydroxy stearate, calcium laurate, barium laurate or zinc laurate, or coconut oil, palm nucleus oil, herring oil, cod-liver oil, whale oil, palm oil, cottonseed oil, olive oil, peanut oil, soybean oil, linseed oil, castor oil and hardened oil that these oils are hydrogenated.

The resin composition of the present invention may contain further, for example, commonly used additives, such as antioxidants, light stabilizers or metal deactivators, or optionally several fillers or electrically-conductive powders, etc.

The antioxidants that may be added besides phosphazenes of the present invention include, for example, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tertt-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-dinonyl-4-methylphenol, 2,6-di-tert-butyl-4-methoxymethylphenol, 2,4-dimethyl-6-(1'-methyl-undeca-1'-yl)-phenol, 2,4-dimethyl-6-(1'-methyl-trideca-1'-yl)-phenol and a mixture thereof, 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol and a mixture thereof, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate and a mixture thereof, 2,4-bis-octylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,3,5triaziene, 1,3,5-tris(3,5di-tert-butyl-4-hydroxybenzyl)-isocyanurate, 1,3,5-tris(4-tert-butyl-3-hydroxy-2,6-dimethylbenzyl)-isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)-isocyanurate, etc. and 2,2'-methylenebis(6-tert-butyl-4-methylphenol), 2,2'-methylenebis(6-tert-butyl-4-ethylphenol, 2,2'-ethylidenebis(4,6-di-tert-butylphenol), 2,2'-ethylidenebis(6-tert-butyl-4-isobutylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, ethylene glycol bis[3,3'-bis(3'-tert-butyl-4'-hydroxyphenyl)butyrate], and 1,3,5-tris(3,5-di-tert-butyl-4-hydroxybenzyl)-2,4,6trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)-phenol, and the like.

The light stabilizers that may be added besides phosphazenes of the present invention include, for example, 2-(2'-hydroxy-5'-methylphenyl)benzotriazole, 2-(3',5'-di-tert-butyl-2-hydroxyphenyl)benzotriazole, 2-(5'-tert-butyl-2'-hydroxyphenyl) benzotriazole, 2-[2'-hydroxy-5'-(1,1,3,3- tetramethylbutyl)phenyl]benzotriazole, 2-(3',5'-di-tert-butyl-2'-hydroxyphenol)-5-chlorobenzotriazole, 2-(3'-tert-butyl-2'-hydroxy-5'-methylphenyl)-5-chlorobenzotriazole, 2-(2'-hydroxy-4'-octoxyphenyl)benzotriazole, 2-(3',5'-di-tert-amyl-2'-hydroxyphenyl)benzotriazole, 2-[3'-tert-butyl-2'-hydroxy-5'-(2'octyloxycarbonylethylphenyl)]-5-chlorobenzotriazole etc.; 4-hydroxy-, 4-methoxy-, 4-octoxy-, 4-decyloxy-, 4-dodecyloxy-, 4-benzyloxy-, 4,2',4'-trihydroxy-, 2'-hydroxy-4,4'-dimethoxy- or 4-(2-ethylhexyloxy)-2-hydroxybenzophenone derivative, etc.; 4-tert-butylphenyl salicylate, phenyl salicylate, octylphenyl salicylate, dibenzoyl resorcinol, bis(4-tert-butylbenzoyl resorcinol), 2,4-di-tert-butylphenyl resorcinol, 3,5-di-tert-butyl-4-hydroxy benzoate, hexadecyl-3,5-di-tert-butyl-4-hydroxy benzoate, etc.; ethyl α-cyano-β,β-diphenyl acrylate, isooctyl α-cyano-β,β-diphenyl acrylate, methyl α-carbomethoxy cinnamate, methyl α-cyano-β-methyl-p-methoxy cinnamate, etc.; bis(2,2,6,6-tetramethyl-4-piperidyl)sebacate, bis(2,2,6,6-tetramethyl-4-piperidyl) saccinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) adipate, etc.; 4,4'-dioctyloxyoxanilide, 2,2'-diethoxyoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxanilide, 2-ethoxy-5-tert-butyl-2'-ethoxyoxanilide, etc.; 2,4,6-tris(2-hydroxy-4-octyloxyphenyl)-1,3,5-triazine, 2-(2-hydroxy-4-octyloxyphenyl)-4,6-bis(2,4dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-dodecyloxyphenyl)-4,6-bis(2,4-dimethylphenyl)-1,3,5-tiazine, etc.

The metal deactivators that may be added besides phosphazenes of the present invention include, for example, N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,3-triazole, bis(benzylidene)oxalic hydrazide, isophthalic dihydrazide, N,N'-diacetal-adipic dihydrazide, N,N'-bissalicyloyloxalic dihydrazide, N,N'-bissalicyloylthiopropionic dihydrazide, etc.

The resins constituting the resin composition containing the phosphazene compositions of the present invention include, for example, polyethylene, polypropylene, ethylene-propylene copolymer, polybutylene, polymethylpenten, ethylene-vinyl acetate copolymer, ethylene-methyl (ethyl) acrylate copolymer, AS resin, ABS resin, PC resin, PC-ABS alloy, polystyrene, PET, PC-PET alloy, polyphenylene ether resin, polyphenylene sulfide resin, polybutadiene resin, polybutylene terephthalate resin, methacrylic resin, polyamide resin, epoxy resin, diallylphthalate resin, silicone resin, unsaturated polyester, etc.

The resin composition of the present invention is used for producing several molded articles, and particularly useful as materials for producing coatings, in particular, fireproof protective coatings for wires, cables, electric components, mechanical components, plugs, mounts, casings, covers or housings.

BEST MODE FOR CARRYING OUT THE INVENTION

Hereinafter, the present invention is concretely described based on examples, however it should be understood that the invention is not necessarily limited thereto. In the meantime, "unit" in "unit mol" in the examples means $PNCl_2$ and 1 unit mol corresponds to 115.87 g. Percentage (%) is by weight (% by weight) other than yield.

The quantity of halogen in obtained phosphazenes was analyzed by coulometric titration method. In the coulometric titration method, the content of halogen was determined by pyrolytically decomposing the resulting phosphazene, capturing in a absorbing liquid in a form of hydrogen halide and measuring electrical quantity required for obtaining silver halide by electrolysis of the halide and silver equivalent to halogen.

EXAMPLE 1

A 1-L flask was equipped with a stirrer, thermometer, receiver of fractional distillation for measurement of moisture content and reflux condenser. The flask was charged with 87.5 g (1.05 mol) of 48% NaOH, 220 mL of toluene and 98.8 g (1.05 mol) of phenol. The mixture was subjected to azeotropic dehydration by heating with stirring (recovered water: 64 mL) to remove moisture in the flask, and then Na (sodium) salt of phenol was formed. Then, the mixture was cooled to 80° C., 25.0 g (0.342 mol) of N,N-dimethylformamide was added and a toluene solution of hexachlorophosphazene (58.0 g (0.16 mol) of compound of general formula (3) wherein m is 3, and 275 mL of toluene) was added dropwise at 80° C. with stirring for 2 hours, and stirred and reacted at the same temperature for 10 hours. After the reaction was completed, 200 mL of water was added into the flask to dissolve inorganic salt, and then the organic layer was separated with a separatory funnel. The organic layer was neutralized and washed with water, and toluene was recovered at atmospheric pressure to 130° C. (in this case remaining toluene was 54 mL). The mixture was cooled to 60° C., and after adding 100 mL of methanol cooled gradually to 5° C., and separated crystals were filtered to obtain 107.7 g of hexaphosphazenes being the aimed compounds. The obtained hexaphosphazenes were analyzed in the purity with HPLC and confirmed that they were composed of 100.00% by weight of hexaphenoxyphosphazene and 0.00% by weight of linear phenoxyphosphazene.

COMPARATIVE EXAMPLE 1

The reaction was carried out similarly to Example 1. After the reaction was completed, 200 mL of water was added into the flask to dissolve inorganic salt, and then the organic layer was separated with a separatory funnel. The organic layer was neutralized with 75% sulfuric acid, washed with water, and toluene was distillated off to obtain 113.4 g of hexaphenoxyphosphazenes as pale yellow crystals. The obtained hexaphenoxyphosphazenes were analyzed in the purity with HPLC and confirmed that they were composed of 94.44% by weight of hexaphenoxyphosphazene and 5.56% by weight of linear phenoxyphosphazene. In addition, the chlorine analysis of the resulting phenoxyphosphazene composition by coulometric titration method indicated that the halogen content thereof was 60 ppm.

This Comparative Example 1 shows that the conventional method in which a cyclic raw material wherein m is 3 and Q is a halogen in general formula (1) is used provides also linear phenoxyphosphazenes.

COMPARATIVE EXAMPLE 2

The reaction was carried out in similar conditions as Comparative Example 1. The organic layer was neutralized and washed with water, and toluene was recovered at atmospheric pressure to 130° C. The reaction mixture was cooled to 60° C., and after adding 100 mL of methanol cooled gradually to 5° C., and separated crystals were filtered to obtain 107.7 g of hexaphosphazenes being the aimed compounds. The halogen content of the resulting phosphazenes was 60 ppm.

COMPARATIVE EXAMPLE 3

Tetrahydrofuran and 42.0 g (1.05 mol) of 60% NaH were added in a flask equipped with a stirrer, reflux condenser, thermometer and an addition funnel. A solution of 98.8 g (1.05 mol) of phenol diluted with 180 mL of tetrahydrofuran was added dropwise through the addition funnel. After the conclusion of the dropwise addition, the mixture was heated and stirred at 40° C. for 30 minutes. Then, the temperature was returned to a room temperature. The tetrahydrofuran solution of the resulting Na salt of phenol was subjected to the next reaction at once. To a 1-L flask equipped with a stirrer, reflux condenser, thermometer and an addition funnel, 600 mL of tetrahydrofuran and 58.0 g (0.167 mol) of hexachlorophosphazene (compound of general formula (3) wherein m is 3) were added and stirred at a room temperature. After hexachlorophosphazene was completely dissolved, the tetrahydrofuran solution of Na salt of phenol was gradually added dropwise through the addition funnel. After the conclusion of the dropwise addition, the reaction mixture was stirred for 24 hours. After the reaction was completed, the mixture was cooled and insoluble material was filtered out. The filtrate was condensed, and crystallized from water/acetone to obtain 107.7 g of hexaphenoxyphosphazenes. The halogen content of the obtained phosphazenes were 5760 ppm.

EXAMPLE 2

A 1-L flask was equipped with a stirrer, thermometer, receiver of fractional distillation for measurement of moisture content and reflux condenser. The flask was charged with 87.5 g (1.05 mol) of 48% NaOH, 220 mL of toluene and 98.8 g (1.05 mol) of phenol. The mixture was subjected to azeotropic dehydration by heating with stirring (recovered water: 64 mL) to remove moisture in the flask, and then Na (sodium) salt of phenol was formed. Then, the mixture was cooled to 80° C., 25.0 g (0.342 mol) of N,N-dimethylformamide was added and a toluene solution of chlorophosphazene mixture (to 275 mL of toluene was dissolved 58.0 g (0.5 unit mol) of a chlorophosphazene mixture comprising 60.8% compound of general formula (3) wherein m is 3; 21.2% compound of general formula (3) wherein m is 4; 6.2% compound of general formula (3) wherein m is 5 or more; and 11.8% linear phosphazenes of general formula (4)) was added dropwise at 80° C. with stirring for 2 hours, and stirred and reacted at the same temperature for 10 hours. After the conclusion of the reaction, 200 mL of water was added into the flask to dissolve inorganic salt, and then the organic layer was separated with a separatory funnel. The organic layer was neutralized with 75% sulfuric acid and washed with water, and toluene was distilled off to obtain 112.9 g of phenoxyphosphazene mixture in a form of brown wax. A 1-L flask equipped with a stirrer, thermometer and condenser was charged with 112.9 g of the obtained phenoxyphosphazene mixture, 50 mL of toluene and 200 mL of methanol, the temperature was raised to 65° C., and insoluble materials were filtered off under heating. The obtained filtrate was crystallized by cooling gradually to 5° C. to obtain 95.8 g of cyclic phenoxyphosphazenes. The obtained phenoxyphosphazenes were analyzed in the purity with HPLC and confirmed that they were composed of 72.38% by weight of hexaphenoxyphosphazene, 24.51% by weight of octaphenoxyphosphazenes, 3.10% by weight of phenoxyphosphazenes of m=5 or more and 0.01% by weight of linear phenoxyphosphazene. Further, the chlorine analysis of the resulting phenoxyphosphazenene composition by coulometric titration method indicated that the halogen content thereof was 5 ppm.

EXAMPLE 3

Chlorophosphazene mixture (55.4% compound of general formula (3) wherein m is 3; 14.6% compound of general formula (3) wherein m is 4; 8.2% compound of general formula (3) wherein m is 5 or more; and 21.8% linear phosphazenes of general formula (4)) was used instead of chlorophosphazene mixture (60.8% compound of general formula (3) wherein m is 3; 21.2% compound of general formula (3) wherein m is 4; 6.2% compound of general formula (3) wherein m is 5 or more; and 11.8% linear phosphazenes of general formula (4)) in Example 2, and reacted under similar conditions as those in Example 2. As a result of it, 84.1 g of cyclic phenoxyphosphazenes. The obtained phosphazenes were analyzed in the purity with HPLC and confirmed that they were composed of 74.03% by weight of hexaphenoxyphosphazene, 19.04% by weight of octaphenoxyphosphazenes, 6.89% by weight of phenoxyphosphazenes of m=5 or more and 0.04% by weight of linear phenoxyphosphazene. Further, the chlorine analysis of the resulting phenoxyphosphazenene composition by coulometric titration method indicated that the halogen content thereof was 3 ppm.

EXAMPLE 4

Chlorophosphazene mixture (74.7% compound of general formula (3) wherein m is 3; 9.9% compound of general formula (3) wherein m is 4; 11.8% compound of general formula (3) wherein m is 5 or more; and 2.6% linear phosphazenes of general formula (4)) was used instead of chlorophosphazene mixture (60.8% compound of general formula (3) wherein m is 3; 21.2% compound of general formula (3) wherein m is 4; 6.2% compound of general formula (3) wherein m is 5 or more; and 11.8% linear phosphazenes of general formula (4)) in Example 2, and reacted under similar conditions as those in Example 2. As a result of it, 108.6 g of cyclic phenoxyphosphazenes. The obtained phosphazenes were analyzed in the purity with HPLC and confirmed that they were composed of 81.30% by weight of hexaphenoxyphosphazene, 10.47% by weight of octaphenoxyphosphazenes, 8.23% by weight of phenoxyphosphazenes of m=5 or more and 0.00% by weight of linear phenoxyphosphazene. Further, the chlorine analysis of the resulting phenoxyphosphazenene composition by coulometric titration method indicated that the halogen content thereof was 10 ppm.

EXAMPLE 5

113.5 g of p-cresol was used instead of 98.8 g of phenol in Example 2, and reacted under similar conditions as those in Example 2. As a result of it, 105.8 g of cyclic p-tolyloxyphosphazene composition. The obtained phosphazenes were analyzed in the purity with HPLC and confirmed that they were composed of 73.44% by weight of hexa p-tolyloxyphosphazene, 22.98% by weight of octa p-tolyloxyphosphazenes, 3.57% by weight of p-tolyloxyphosphazenes of m=5 or more and 0.01% by weight of linear p-tolyloxyphosphazene. Further, the chlorine analysis of the obtained p-tolyloxyphosphazene composition by coulometric titration method indicated that the halogen content thereof was 8 ppm.

EXAMPLE 6

A mixer was charged with 10.0% by weight of the cyclic phenoxyphosphazenes obtained in Example 1 and 90.0% by weight of polypropylene as a polyolefin resin, and kneaded at 180° C. to obtain a mixture. The obtained mixture was formed into a sheet with a compression molding press (185° C., 3 minutes), and the obtained sheet was subjected to an assessment of flame retardance. The results are shown in Table 1.

EXAMPLES 7 TO 10

Phosphazene compositions obtained in Examples 2 to 5 were used instead of the phenoxyphosphazene obtained in Example 1, and subjected to an assessment of flame retardance in a similar manner as that in Example 6. The results are shown in Table 1.

COMPARATIVE EXAMPLE 4

The phosphazene composition obtained in Comparative Example 1 was used instead of the phenoxyphosphazene obtained in Example 1, and subjected to an assessment of flame retardance in a similar manner as that in Example 6. The results are shown in Table 1.

TABLE 1

The results of assessment of flame retardance

| | Oxygen Index |
|---|---|
| Example 6 | 26.5 |
| Example 7 | 26.1 |
| Example 8 | 25.8 |
| Example 9 | 26.3 |
| Example 10 | 25.7 |
| Comparative Example 4 | 22.3 |

The oxygen index means the minimum oxygen concentration (% by volume) to support combustion of a material. For example, a sample having an oxygen index of 25.0 behaves as follows: it burns on an ignition in an atmosphere having an oxygen concentration of 25.0% or more, and self-extinguishes in an atmosphere having an oxygen concentration of 25.0% or less (hereinafter this is applied similarly). Taking into account what oxygen concentration of the atmosphere is ca. 20.9%, materials having oxygen index over 20.9 self-extinguish under natural surroundings, and therefore are high in flame retardant effect.

EXAMPLE 11

A mixer was charged with 3.2% by weight of the cyclic phenoxyphosphazenes obtained in Example 2, 32.3% by weight of magnesium hydroxide and 64.5% by weight of polypropylene as a polyolefin resin, and kneaded at 180° C. to obtain a mixture. The obtained mixture was formed into a sheet with a compression molding press (185° C., 3 minutes), and the obtained sheet was subjected to an assessment of flame retardance. The results are shown in Table 2.

EXAMPLES 12 TO 14

Phosphazene compositions obtained in Examples 2 to 5 were used instead of the phenoxyphosphazene obtained in Example 2, and subjected to an assessment of flame retardance in a similar manner as that in Example 11. The results are shown in Table 2.

COMPARATIVE EXAMPLE 5

Only magnesium hydroxide was added without adding phosphazenes obtained in Example 2, and subjected to an assessment of flame retardance in a similar manner as that in Example 11. The results are shown in Table 2.

TABLE 2

The results of assessment of flame retardance

| | Oxygen Index |
|---|---|
| Example 11 | 30.4 |
| Example 12 | 30.3 |
| Example 13 | 30.4 |
| Example 14 | 30.2 |
| Comparative Example 5 | 23.0 |

EXAMPLE 15

A mixer was charged with 3.2% by weight of the cyclic phenoxyphosphazene obtained in Example 2 (Sample A) or 3.2% by weight of the cyclic phenoxyphosphazene obtained in Comparative Example 1 (Sample B) in addition to 32.3% by weight of magnesium hydroxide and 64.5% by weight of polyolefin, and sheets were formed therefrom in a similar manner as that in Example 11 to produce test pieces. The produced test pieces were subjected to combustion under the following test conditions under which dioxin tends to be produced, and the amount of dioxin in waste gas was measured (based on JIS K 0311). The results are shown in Table 3.

| Test Condition | |
|---|---|
| Furnace in which examples were conducted: | Horizontal tube furnace; |
| Heating rate: | 5° C./min.; |
| Maximum temperature: | 900° C. |
| Time required: | 180 min.; |
| Time maintained at 900° C.: | 60 min.; |
| Supplied gas: | Air (1.17 L/min.); |
| Amount to be tested: | 5.73 g; and |
| Amount of waste gas: | 150.5 NL. |

TABLE 3

Generated amount of dioxins

| | Total PCDDs Toxicity Equivalent Quotient (TEQ) ng/g-dry | Total PCDDs Toxicity Equivalent Quotient (TEQ) ng/g-dry |
|---|---|---|
| Sample A | less than 0.001 (out of detection limit) | less than 0.001 (out of detection limit) |
| Sample B | 0.132 | 0.156 |

The analysis of dioxins generated in the combustion of Sample A indicated that 2,3,7,8-tetrachlorodibenzo-p-dioxin (2,3,7,8-TeCDD), 1,2,3,7,8-pentachlorodibenzo-p-dioxin (1,2,3,7,8-PeCDD) and 2,3,4,7,8-pentachlorodibenzofuran (2,3,4,7,8-PeCDF) that have a strong toxicity were less than the detection lower limit. On the contrary, the analysis of dioxins generated in the combustion of Sample B indicated that 2,3,7,8-tetrachlorodibenzo-p-dioxin (2,3,7,8-TeCDD), 1,2,3,7,8-pentachlorodibenzo-p-dioxin (1,2,3,7,8-PeCDD) and 2,3,4,7,8-pentachlorodibenzofuran (2,3,4,7,8-PeCDF) that have a strong toxicity were present in amounts of 0.009 ng/g-dry, 0.069 ng/g-dry and 0.10 ng/g-dry, respectively, and that total PCDDs toxicity equivalent quotient (ng/g-dry) and total PCDFs toxicity equivalent quotient (ng/g-dry) were values shown in Table 3.

Consequently, the phenoxyphosphazenes of the present invention can be said to be flame retardants good for the environment because they generate a slight amounts of dioxins even combustion condition under which dioxins tend to be generated. In the table, toxicity equivalent quotient (TEQ) is 2,3,7,8-tetrachlorodibenzo-p-dioxin (2,3,7,8-TeCDD) toxicity equivalent quotient and means the value determined by converting the amount of generated dioxins to 2,3,7,8-TeCDD toxicity. In addition, PCDDs and PCDFs mean polychlorodibenzo-p-dioxines and polychlorodibenzofurans, respectively, and both of them belong to dioxins.

EFFECT OF THE INVENTION

The effects of the present invention are as follows:
(1) The present invention can provide cyclic phosphazenes having a halogen content of as low as 50 ppm or less, that is being substantially free from halogen although halogen containing compounds are used as a raw material. Therefore, resins containing the phosphazenes as a flame retardant do not generate dioxins even when they are subjected to combustion.
(2) The present invention can provide cyclic phosphazenes with a high purity, the linear phosphazenes content of which is 5.0% by weight or less, preferably 1.0% by weight, particularly preferably 0.1% by weight, without repeated purification.
(3) When the flame retardants containing cyclic phosphazenes of the present invention is compared with those containing linear phosphazenes in an amount of 5.0% by weight or more, the former is by far excellent in flameproof effect.

The invention claimed is:

1. A flame retardant containing a composition as an active ingredient, the composition comprising:
cyclic phosphazenes of general formula (1)

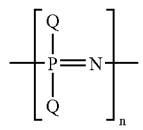

(2)

wherein Q is a halogen and/or an aryloxy group, and m is an integer of 3 to 10, which are characterized by being substantially free from linear phosphazenes of general formula (2)

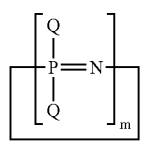

(1)

wherein Q is a halogen and/or an aryloxy group, and n is an integer of 1 to 20.

2. A flame retardant containing a composition as an active ingredient, the composition comprising:
cyclic phosphazenes of general formula (1)

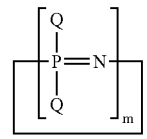

(1)

wherein Q is a halogen and/or an aryloxy group, and m is an integer of 3 to 10, which are produced by separating and purifying a phosphazene composition comprising the cyclic phosphazenes of general formula (1) and linear phosphazenes of general formula (2)

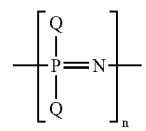

(2)

wherein Q is a halogen and/or an aryloxy group, and n is an integer of 1 to 20.

3. The flame retardant according to claim 1, wherein Q in general formula (1) is an aryloxy and the cyclic phosphazenes are substantially free from halogen.

4. The flame retardant according to claim 3, wherein a content of the halogen is 50 ppm or less.

5. A process for preparing the flame retardant containing the composition comprising the cyclic phosphazenes according to claim 1, characterized by separating and purifying cyclic phosphazenes of general formula (1)

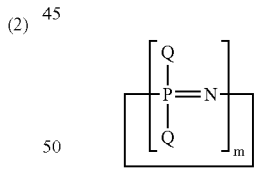

(1)

wherein Q is a halogen and/or an aryloxy group, and m is an integer of 3 to 10, by crystallization from a phosphazene composition comprising the cyclic phosphazenes of general formula (1) and linear phosphazenes of general formula (2)

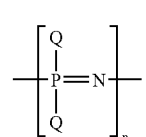

(2)

wherein Q is a halogen and/or an aryloxy group, and n is an integer of 1 to 20.

6. A process for preparing the flame retardant containing the composition comprising the cyclic phosphazenes according to claim 3, characterized by separating and purifying cyclic phosphazenes of general formula (1)

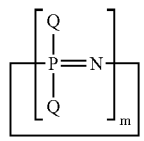
(1)

wherein Q is a halogen and/or an aryloxy group, and m is an integer of 3 to 10, by crystallization from a phosphazene composition comprising the cyclic phosphazenes of general formula (1) and linear phosphazenes of general formula (2)

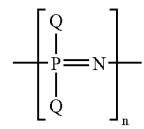
(2)

wherein Q is a halogen and/or an aryloxy, and n is an integer of 1 to 20.

7. A resin composition characterized by containing the flame retardant according to claim 1.

8. A molded article characterized by being molded from the resin composition according to claim 7.

9. The flame retardant according to claim 1, prepared by crystallizing a mixture of cyclic and linear aryloxyphosphazenes in a solvent containing aromatic non-polar solvent.

10. The process according to claim 5, wherein the crystallization is carried out in a solvent containing aromatic non-polar solvent.

* * * * *